United States Patent [19]

Fujiwhara et al.

[11] 3,938,996
[45] Feb. 17, 1976

[54] PROCESS FOR DEVELOPING LIGHT-SENSITIVE SILVER HALIDE PHOTOGRAPHIC MATERIALS

[75] Inventors: Mitsuto Fujiwhara; Ryosuke Satoh; Toyoaki Masukawa; Takahiro Uozumi, all of Hino, Japan

[73] Assignee: Konishiroku Photo Industry Co. Ltd., Tokyo, Japan

[22] Filed: June 17, 1974

[21] Appl. No.: 479,895

[30] Foreign Application Priority Data

June 22, 1973  Japan.............................. 48-69867

[52] U.S. Cl. .......................... 96/66.3; 96/3; 96/95
[51] Int. Cl.$^2$ .................... G03C 5/30; G03C 7/00
[58] Field of Search.......................... 96/66.3, 3, 95

[56] References Cited
UNITED STATES PATENTS

| | | | |
|---|---|---|---|
| 3,364,022 | 1/1968 | Barr | 96/66.3 |
| 3,537,851 | 11/1970 | Bloom | 96/3 |
| 3,537,852 | 11/1970 | Bloom | 96/3 |
| 3,620,746 | 11/1971 | Barr | 96/3 |

Primary Examiner—Mary F. Kelley
Attorney, Agent, or Firm—Jordan B. Bierman; Linda G. Bierman; Kenneth J. Stempler

[57] ABSTRACT

This invention relates to a development inhibitor-releasing compound of the following general formula:

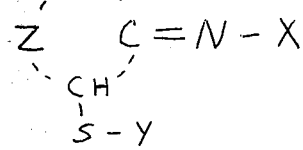

wherein Z is an atomic grouping necessary to form a carbocyclic ring; Y is a group which, when the sulfur atom of the thioether linkage is released, forms together with said sulfur atom a compound having a development-inhibiting action; and X is a hydroxyl group or a substituted or non-substituted amino group.

12 Claims, No Drawings

PROCESS FOR DEVELOPING LIGHT-SENSITIVE SILVER HALIDE PHOTOGRAPHIC MATERIALS

This invention relates to a process for developing a light-sensitive silver halide photographic material, characterized by developing the photographic material in the presence of a novel development inhibitor-releasable compound.

It has heretofore been known to incorporate previously into a light-sensitive photographic material a compound capable of releasing at the time of development a development inhibitor in response to the degree of image density. The said compound (hereinafter referred to as "development inhibitor-releasable compound") is of such a type, in general, that it reacts with the oxidation product of a color developing agent to release a development inhibitor. Typical as such compound is a so-called DIR coupler incorporated at the active center thereof with a group capable of forming, when released from the active center, a compound showing a development-inhibiting action. The said coupler has such properties that when coupled with the oxidation product of a color developing agent, the coupler body forms a dye and, on the other hand, releases a development inhibitor.

The development inhibitor-releasable compound is used, in general, for such purposes as mentioned below.

That is, the development inhibitor-releasable compound characteristically releases at the time of development a development inhibitor in response to the degree of image density, and the thus released development inhibitor, when it is in an emulsion layer, inhibits the development of said layer in response to the degree of image density. Accordingly, the compound is used in expectation of mainly such two kinds of image effects as the so-called intra-image effects such as image tone control, improved graininess of image and improved sharpness of image; and, when the said development inhibitor has diffused to other layer, the so-called inter-image effects such as masking action to inhibit the development of said other layer in response to the degree of image density of the layer as the source of diffusion, and color hue derived from inhibition of development of other layer in the case of monochromatic light exposure or the like.

While various development inhibitor-releasable compounds have been known hitherto, these are still unsatisfactory for the above-mentioned expectation. For example, some of them form dyes at the time of color development, so that turbid images are obtained unless the hues of said dyes are carefully selected, or no desirable inhibition effect can be attained when the hues of said dyes have been properly selected, or the compounds are entirely non-compatible depending on the kinds of photographic materials, while even in the case of other compounds which form no dyes, they are low in reactivity with the oxidation products of color developing agents, and hence are required to be added in large quantities to cause such disadvantages that the photographic materials are deteriorated in photographic properties (e.g. speed) or in storability, or they cannot give sufficient development-inhibiting effects when used in small amounts.

In the present invention, a specific compound is used as the development inhibitor-releasable compound to overcome the above-mentioned disadvantages of the prior art, and thus the resulting image has excellent properties due to the excellent intra-image effects and inter-image effects provided by the said compound.

The development inhibitor-releasable compound used in the present invention is a compound, which not only forms a substantially colorless compound by reaction with the oxidation product of a color developing agent but also releases a development inhibitor, and is represented by the following general formula:

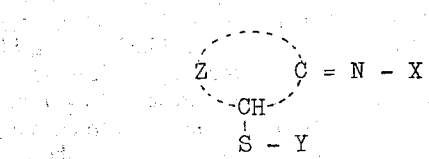

wherein Z is an atomic grouping necessary to form the carbocyclic ring; Y is a group which, when the sulfur atom of the thioether linkage is released, forms together with said sulfur atom a compound having a developmentinhibiting action; and X is a hydroxyl group or a substituted or non-substituted amino group.

The compound used in the present invention forms a colorless compound when reacted with the oxidation product of a color developing agent. Since the thus formed compound does not constitute any part of the final image, no other compound different in construction from that used in the present invention is required to be additionally used according to the kind of layer or the like application purpose. Thus, the compound used in the present invention has such advantage that it can be applied singly to any layers or any photographic materials. Further, the compound is highly reactive with the oxidation product of a color developing agent, and therefore the use of a small amount of the compound can advantageously give excellent intra-image and inter-image effects.

Depending on the kind of the carbocyclic ring in the aforesaid general formula, or of the substituent introduced therein, the development inhibitor-releasable compound used in the present invention may advantageously be selected, so as to be suitable for its application purpose, from various diffusible and non-diffusible compounds. For example, a diffusible compound may be incorporated into optional constitutive layers of a color photographic material, and, in extreme cases, may be incorporated into only one layer to inhibit the development of all layers, whereby the individual layers can be inhibited from development by the development-inhibiting effect imparted to said single layer, though more or less difference is seen between them. Furthermore, a diffusible compound may be incorporated also into a color developing agent. On the other hand, a non-diffusible compound is useful when intra-image and inter-image effects are desired to be imparted to only specific layers, and may be used, for example, to provide some difference in characteristic with individual layers.

Typical as such development inhibitor-releasable compounds are those of the aforesaid general formula, wherein Z is, for example, a 5-, 6- or 7-membered, saturated or unsaturated carbocyclic ring, whose concrete and typical examples are cyclopentanone, cyclohexanone and cyclohexenone. These carbocyclic rings include those having at least one of such substituents as alkyl groups, aryl groups, alkoxy groups, aryloxy groups and halogens, and those which have formed at a suitable position any of such condensed rings as, for example, indanone, benzocyclohexenone and benzocycloheptenone, which condensed rings may have the above-mentioned substituents. Further, the carbocyclic rings may have at the carbon adjacent to the carbonyl group at least one of -SY group (wherein Y is as defined previously). On the other hand, Y in the aforesaid formula is a group which, when the sulfur atom of the thioether linkage is released, forms together with said sulfur atom a compound having a development-inhibiting action, and is, for example, an allylmercapto compound, a heterocyclic compound, a thioglycolic acid series compound, cystein or glutathione. Typical examples of the mercapto compound represented by Y include heterocyclic mercapto compounds, such as mercaptotetrazole type compounds, particularly, 1-phenyl-2-mercaptotetrazole, 1-nitrophenyl-5-mercaptotetrazole and 1-naphthyl-5-mercaptotetrazole, mercaptothiazole type compounds, particularly 2-mercaptobenzothiazole and mercaptonaphthothiazole; mercaptooxadiazole type compounds; mercaptopiperidine type compounds; mercaptothiadiazole type compounds, particularly 2-mercaptothiadiazolotriazone; mercaptotriazine type compounds; mercaptotriazole type compounds; and mercaptobenzene type compounds, particularly 1-mercapto-2-benzoic acid, 1-mercapto-2-nitrobenzene and 1-mercapto-3-heptadecanoylaminobenzene. Further, X in the aforesaid formula is a hydroxyl group or a substituted or unsubstituted amino group, and is typically an X group in a compound having the formula of the type C=N—X which is easily formed by the dehydrogenation reaction of a ketone group with a carbonyl reagent of the formula $H_2N$-X. Examples of the compound of the formula $H_2N$-X are hydroxylamines, hydrazinesemicarbazides and thiosemicarbazides. Concrete examples of the hydrazines include hydrazine, phenylhydrazine, substituted phenylhydrazines having in the phenyl any of such substituents as alkyl groups, aryl groups, alkoxy groups, carboalkoxy groups and halogens, and isonicotinic acid hydrazide; concrete examples of the semicarbazides include phenylsemicarbazide, and substituted phenylsemicarbazides having any of such substituents as alkyl groups, alkoxy groups, carboalkoxy groups and halogens; and concrete examples of the thiosemicarbazides include derivatives similar to those in the case of the semicarbazides.

Typical examples of the development inhibitor-releasable compounds having the aforesaid general formula are as follows:

(1) 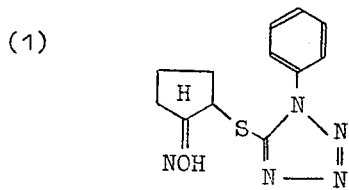

(2) 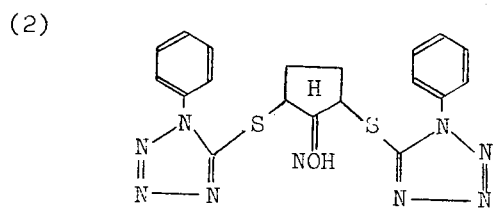

(3) 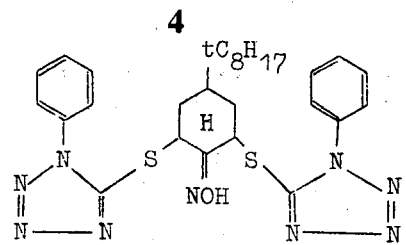

(4) 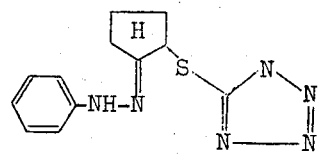

(5) 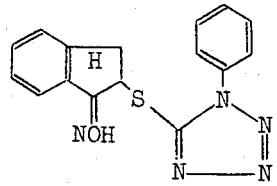

(6) 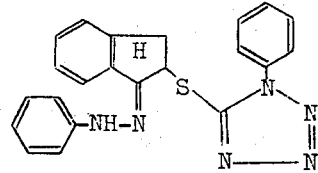

(7) 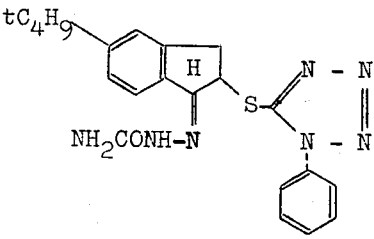

(8) 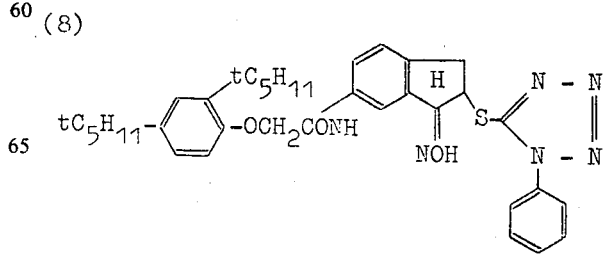

(9) 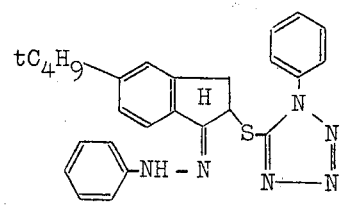

(10) 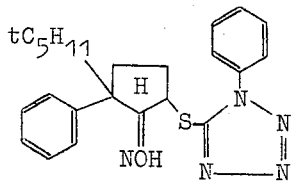

(11) 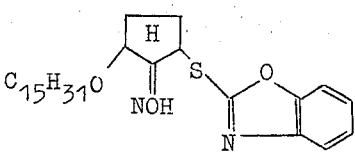

(12) 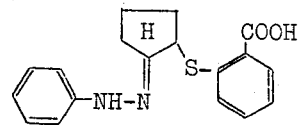

(13) 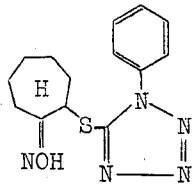

(14) 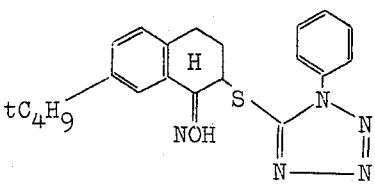

(15) 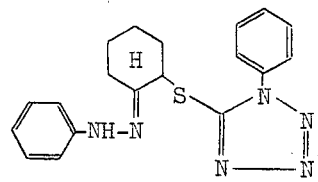

(16) 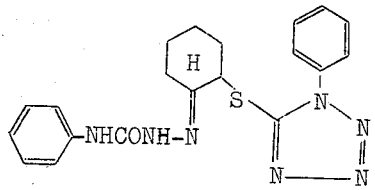

(17) 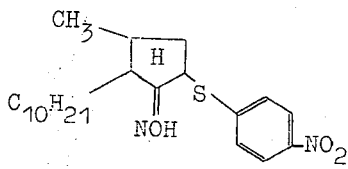

Typical procedures for synthesizing some of the above-mentioned compounds are shown below with reference to synthesis examples, and other compounds can also be synthesized according to these examples.

SYNTHESIS EXAMPLE 1

Synthesis of the compound (2)

A mixture comprising 5 g. of 2,5-di-(1-phenyl-5-tetrazolylthio)-cyclopentanone, 3.6 g. of hydroxylamine hydrochloride and 10 ml. of pyridine was heated with reflux for 4 hours in 250 ml. of 95 percent alcohol. The liquid reaction mixture was poured into water, extracted with ethyl acetate, concentrated, dissolved in benzene at an elevated temperature and then allowed to stand to deposit the compound (2) as white crystals, m.p. 103°–105°C., yield 4 g.

SYNTHESIS EXAMPLE 2

Synthesis of the compound (5)

A mixture comprising 1.4 g. of 2-(1-phenyl-5-tetrazolylthio)indanone-1, 1.4 g. of hydroxylamine hydrochloride and 2 ml. of pyridine was heated with reflux for 4 hours in 70 ml. of 95 percent alcohol. The liquid reaction mixture was poured into water, extracted with ethyl acetate, concentrated and then recrystallized from benzene to obtain the compound (5) as white crystals, m.p. 150°–152°C., yield 0.7 g.

SYNTHESIS EXAMPLE 3

Synthesis of the compound (6)

A mixture comprising 1 g. of phenylhydrazine, 0.5 g. of 2-(1-phenyl-5-tetrazolylthio(indanone-1 and a small amount of methanol was heated for about 20 minutes in a water bath at 95°C. After cooling, the liquid reaction mixture was solidified by addition of hexane, filtered and then recrystallized from methanol to obtain the compound (6) as pale yellow crystals, m.p. 235°–238°C., yield 0.3 g.

Sulfur contents, as measured by elementary analysis, of the compounds (1) to (17) synthesized in the above-mentioned manner are as shown below.

| Compound | Molecular formula | Elementary analysis (S) | |
|---|---|---|---|
| | | Calculated (%) | Found (%) |
| (1) | $C_{12}H_{13}N_5OS$ | 11.64 | 11.81 |
| (2) | $C_{19}H_{17}N_9OS_2$ | 14.19 | 14.03 |
| (3) | $C_{29}H_{34}N_9OS_2$ | 11.12 | 11.38 |
| (4) | $C_{18}H_{18}N_6S$ | 9.14 | 9.28 |
| (5) | $C_{16}H_{13}N_5OS$ | 9.91 | 9.85 |
| (6) | $C_{22}H_{18}N_6S$ | 8.04 | 8.27 |
| (7) | $C_{21}H_{23}N_7OS$ | 7.61 | 7.38 |
| (8) | $C_{34}H_{40}N_6O_3S$ | 5.23 | 5.62 |
| (9) | $C_{26}H_{26}N_6S$ | 7.05 | 7.02 |
| (10) | $C_{23}H_{27}N_5OS$ | 7.61 | 7.47 |
| (11) | $C_{27}H_{42}N_2O_3S$ | 6.75 | 6.98 |
| (12) | $C_{18}H_{18}N_2O_2S$ | 9.82 | 10.01 |
| (13) | $C_{14}H_{17}N_5OS$ | 10.57 | 10.77 |
| (14) | $C_{21}H_{23}N_5OS$ | 8.15 | 8.02 |
| (15) | $C_{19}H_{20}N_6S$ | 8.80 | 8.92 |
| (16) | $C_{20}H_{21}N_7OS$ | 7.87 | 7.91 |
| (17) | $C_{22}H_{32}N_2O_3S$ | 7.73 | 7.72 |

The compounds of the aforesaid general formula which are synthesized in the manner described above can be used in various light-sensitive silver halide photographic materials. For example, they are useful for any of black-white, color and pseudo-color photographic materials and can be applied to light-sensitive silver halide photographic materials to be used as general black-white, printing black-white, X-ray, electron-ray, high resolution black-white, general color, X-ray color, diffusion-transfer type color and the like photographic materials. The silver halides to be used in the above case are silver chloride, silver bromide, silver iodide and mixed silver halides (e.g. silver chlorobromide, silver iodobromide, silver chloroiodobromide, etc.), which may have been prepared according to any process, e.g. so-called conversion process or Lippmann process, and vary depending on the kinds of photographic materials. Further, the particle size, content and mixing ratio of the silver halides vary depending on the kinds of photographic materials. Generally, silver halides composed mainly of silver chloride are used for photographic materials relatively low in speed, graininess, etc., while silver halides less in content of silver chloride are used for photographic materials relatively high in speed, etc. For use in photographic materials of the direct-positive type, the silver halides are fogged either optically or chemically. Further, the silver halides may be chemically sensitized with one or a mixture of such sensitizers as active gelatin, sulfur sensitizers, e.g. allylthiocarbamide, thiourea and cystine, selenium sensitizers, and noble metal sensitizers such as gold sensitizers, e.g. potassium chloroaurate, potassium aurithiocyanate, potassium chloroaurate and 2-aurosulfobenzothiazole methachloride, or ruthenium, rhodium, palladium and iridium salt sensitizers, e.g. ammonium chloropalladate, potassium chloroplatinate and sodium chloropalladite, which are known to act as sensitizers or antifoggants depending on the amounts thereof.

The silver halides may be applied directly, without using any binder, to supports by vapor deposition or the like to form layers, or may be brought to the form of so-called silver halide emulsions by dispersing in a binder comprising one or more of gelatin, other colloidal substances such as colloidal albumin and cellulose derivatives, and synthetic resins such as polyvinyl compounds, and then applied to supports to the form of layers, if necessary through sub layer, inter layer, etc. The silver halide emulsions may be optically sensitized with, for example, cyanine or merocyanine dyes, and, in a color photographic material, for example, three kinds of silver halide emulsions different in photosensitive wavelength region are used. Further, the emulsions may be stabilized with triazoles, azaindenes, quaternary benzothiazolium compounds, or zinc or cadmium compounds, and may contain quaternary ammonium salt type or polyethylene glycol type sensitizing compounds. The emulsions may further contain various photographic additives, e.g. gelatin plasticizers such as glycerin, 1,5-pentadiol and the like dihydroxyalkanes, ethylenebisglycolic acid esters, bis-ethoxy-diethylenegylycol succinate, amides of acrylic acid-series acids or latexes; gelatin hardeners such as formaldehyde, mucobromic acid and the like halogen-substituted fatty acids, compounds having acid anhydride groups, dicarboxylic acid chlorides, biesters of methanesulfonic acid or sodium bisulfite derivatives of dialdehydes whose aldehyde groups have been separated by 2 or 3 carbon atoms; vehicles such as saponin; and coating aids such as sulfosuccinic acid salts. Particularly when used in internal color photographic materials, the emulsions may contain couplers, e.g. magenta couplers of the 5-pyrazolone type, cyan couplers of the naphthol or phenol type, and yellow couplers having active methylene groups interposed between two carbonyl groups, which couplers may be so-called 2-equivalent or 4-equivalent couplers, or may be so-called masking couplers having, for example, arylazo groups at the active centers. In this case, it is preferable to use so-called colorless couplers, which are colorless before development, in combination with the said masking couplers. In case the couplers used are so-called protect type couplers, for example, the emulsion may contain coupler solvents. Further, the emulsions may contain so-called competing couplers in combination with various couplers in order to enhance the photographic properties. On the other hand, when used in diffusion transfer type color photographic materials, the emulsions may be incorporated with dye developers or coupler developers in place of the couplers. The dye developers referred to in the above are compounds having functions of both dyes and developers which are formed, for example, by introducing hydroquinone, aromatic primary amino color developers, etc. into dyes, while the coupler developers are compounds having functions of both couplers and developers which are formed, for example, by introducing hydroquinone, etc. into or outside the active centers of the aforesaid couplers. When used in color photographic materials for silver dye bleaching method, the emulsions may have previously been incorporated with dyes. Depending on the application purposes of color photographic materials to be obtained, the emulsions may be incorporated, if necessary, with ultraviolet absorbers, fluorescent brighteners, etc.

Such silver halide emulsion as mentioned above is coated on a support to the form of a layer, if necessary through sub layer, inter layer, etc., whereby a light-sensitive silver halide photographic material is obtained. The support used in this case is any of, for example, papers, laminate papers, glass plates, or film or sheets of cellulose acetate, cellulose nitrate, polyester, polyamide or polyester, and is suitably selected according to the application purpose of the photographic material desired to be obtained.

Fundamentally, a light-sensitive silver halide photographic material is composed of a support and a photosensitive layer (silver halide deposit layer or emulsion layer). Depending on its kind, however, the photographic material may additionally have a proper combination of such layers as sub layer, inter layer, filter layer, anti-curling layer and protective layer, as mentioned previously, and the photosensitive layer itself may be composed of a laminate of layers which are high and relatively low, respectively, in sensitivity at same or different wavelength regions, for example. These layers may contain various photographic additives such as those incorporated into the aforesaid emulsions, and may contain additives different in kind depending on the purpose of each layer such that, for example, the filter layer may contain a filter dye, and the protective layer may contain a film property improver, an antistatic agent, etc. Further, in a diffusion transfer type photographic material, for example, there may be provided an inter layer containing physical development nuclei.

When developed in the presence of the compound of the aforesaid general formula, the above-mentioned light-sensitive silver halide photographic material shows such excellent photographic properties as mentioned previously. As an embodiment of the present invention, there is a process in which the said compound is previously incorporated into a photographic material, and this photographic material is subjected to development. In this case, the diffusible compound may be incorporated into any constitutive layers, e.g. into one or more of emulsion layer, inter layer, protective layer, etc., while the non-diffusible compound is desirably incorporated into the emulsion layer or into one or more layers adjacent to the emulsion layer.

In incorporating into each constitutive layer, the said compound may be added in an optional form to a liquid for forming the constitutive layer. For example, the diffusible compound may be added in the form of a solution such as an aqueous alkali solution, while the non-diffusible compound may be added in the form of an emulsion in the aforesaid coupler solvent. Examples of the coupler solvent are water-immiscible high boiling organic solvents such as di-n-butyl phthalate, benzyl phthalate, triphenyl phosphate, tri-o-cresyl phosphate and monophenyl-di-p-t-butylphenyl phosphate. These high boiling organic solvents may be used in admixture with low boiling organic solvents such as, for example, methylisobutylketonen, $\beta$-ethoxyethyl acetate, methoxytriglycol acetate, acetone, methylacetone, methanol, ethanol, acetonitrile, dioxane, dimethylformamide, ethyl acetate, isopropyl acetate and chloroform. The low boiling organic solvents may be used in place of the high boiling organic solvents. These organic solvents may be used either singly or in combination of two or more members.

In another embodiment of the present invention, in which, for example, a diffusion transfer type photographic material is developed in contact with other photographic material such as an image-receiving material, the compound of the aforesaid general formula may be incorporated into said other photographic material. In this case, the said compound is preferably the diffusible compound, in general. However, the non-diffusible compound may also be used in some cases where the said image-receiving material is of such a type that silver halide particles having physical development nuclei are applied to an image-receiving layer (e.g. gelatin layer or polyvinyl compound layer) on a support.

According to another embodiment of the present invention, the compound of the aforesaid general formula may be incorporated into a developer or a pre-processor. Examples of the developer are black-white developers, color developers such as general internal color developers and general external color developers, and, in the case of reversal development, one or both of first and second developers, ordinary black-white developers and X-ray developers; and examples of the pre-processor are prehardeners and the like. The compounds to be incorporated into said developers and pre-processors are desirably the diffusible compounds, in general. In this case, it is also possible that a carrier is previously incorporated into a specific layer of photographic material to emphasize the effect of said layer. Preferably, the above-mentioned modes are carried out in the presence of an aromatic primary amino color developing agent.

As mentioned above, the compounds of the aforesaid general formula can be used in various application modes and, in every case, give more excellent image effects than in the case where the conventional development inhibitor-releasable compounds are used. The effects are particularly marked when the compounds are incorporated into photographic materials.

The amount of the compound used in the present invention varies depending on the application manner, the application purpose and the expected effects, but is preferably 0.1 to 10 g. per kg. of the emulsion. When the compound is used in an amount equal to that of the conventional development inhibitor-releasable compound, the image effects obtained are far greater than in the conventional process. In case the same image effects as in the conventional process are expected to be obtained, the compound may be used in an extremely small amount.

An example of the composition of an external color developer containing the compound of the aforesaid general formula is as follows:

| | |
|---|---|
| Color developing agent | 2 to 8 g. |
| Sodium sulfite (anhydrous) | 1.0 to 6 g. |
| Sodium carbonate (monohydrate) | 40 to 100 g. |
| Potassium bromide | 0.5 to 2 g. |
| Coupler | 0.002 to 0.01 mole |
| Compound of the aforesaid general formula | 1.0 to 5.0 g. |
| Water to make | 1 liter |

Typical composition of an internal color developer is same as above, except that the coupler is excluded. Depending on its application purpose, the internal color developer is not only controlled in pH but also incorporated with other photographic additives.

More concrete examples of the typical compositions of external and internal color developers containing the compounds of the aforesaid general formula are as follows:

| | |
|---|---|
| External color developer: | |
| N-Ethyl-N-p-methanesulfonamidoethyl-3-methyl-4-aminoaniline | 5.0 g. |
| Sodium sulfite | 2.0 g. |
| Benzyl alcohol | 3.5 ml. |
| Sodium carbonate | 82.0 g. |
| Potassium bromide | 1.0 g. |
| Coupler | 0.005 mole |
| Compound of the aforesaid general formula | 2.0 g. |
| Water to make | 1.0 liter |
| Internal color developer: | |
| N-Ethyl-N-$\beta$-methanesulfonamidoethyl-3-methyl-4-aminoaniline sulfate | 5.0 g. |

| | |
|---|---|
| -continued | |
| Sodium sulfite (anhydrous) | 2.0 g. |
| Benzyl alcohol | 3.8 g. |
| Sodium carbonate (monohydrate) | 50.0 g. |
| Potassium bromide | 1.0 g. |
| Potassium hydroxide | 0.55 g. |
| Compound of the aforesaid general formula | 2.5 g. |
| Water to make | 1.0 liter |

Color developing agents used in the present invention are preferably aromatic primary amino compounds, particularly p-phenylenediamine type developing agents such as, for example, N,N-diethyl-p-phenylenediamine, N-ethyl-N-ω-sulfobutyl-p-phenylenediamine, 2-amino-5-diethylaminotoluene and p-amino-N-ethyl-N-β-hydroxyethylaniline. At the time of development of a photographic material, each of the compounds of the aforesaid general formula is desirably made present together with at least one of the above-mentioned color developing agents. Further, a combination of said compounds may be used and, at the same time, a combination of processes according to the present invention may be carried out. As a typical example of such case, there may be shown a process in which the non-diffusible, development inhibitor-releasable compound is incorporated into a specific layer of a photographic material, the diffusible, development inhibitor-releasable compound is incorporated into a processing solution, and the said photographic material is processed with said processing solution.

A photographic material, which has been processed by the development process according to the present invention, may then be subjected to ordinary photographic treatments suitable for the photographic material used which are selected from treatments with, for example, a stopping solution containing an organic acid, a stop-fixing solution containing an organic acid and a fixing component such as ammonium hypo- or thio-sulfate, a fixing solution containing a fixing component such as ammonium hypo- or thio-sulfate, a bleaching solution containing a ferric salt of aminopolycarboxylic acid and an alkali halide as active ingredients, a bleach-fixing solution containing a ferric salt of aminopolycarboxylic acid and a fixing component such as ammonium hypo- or thio-sulfate, and a stabilizing solution, and water-washing, drying and the like treatments.

The present invention is illustrated in further detail below with reference to examples, but the modes of practice of the invention are not limited to the examples.

EXAMPLE 1

Samples I and II were prepared in the following manner:

Sample I

A mixture comprising 2 g. of the compound (10) and 15 g. of a magenta coupler 1-(2,4,6-trichlorophenyl)-3-[3-(2,4-di-tert-amylphenoxyacetamide)benzamide]-5-pyrazolone was dissolved in a solvent comprising 30 cc. of ethyl acetate and 15 cc. of dibutyl phthalate. The resulting solution was mixed with 20 ml. of a 10 percent aqueous Alkanol B (produced by Du Pont Co.) solution and 300 ml. of a 5 percent aqueous gelatin solution. The mixed solution was emulsified and dispersed by means of a colloid mill. The resulting dispersion was dispersed in 1 kg. of a green-sensitive silver iodobromide emulsion, which was then coated on a cellulose triacetate base and dried to prepare the sample I.

Sample II

Entirely the same operation as above was effected, except that the compound (10) was not used, to prepare the sample II as a control.

These two samples I and II were individually exposed through an optical wedge and then developed with a developer of the following composition:

| | |
|---|---|
| N,N-Dimethyl-p-phenylenediamine hydrochloride | 2.0 g. |
| Anhydrous sodium sulfite | 2.0 g. |
| Potassium bromide (monohydrate) | 82.0 g. |
| Water to make | 1.0 liter. |

Subsequently, the samples were subjected to ordinary bleach-fixing to form images composed of a magenta dye. The two samples were same in speed, but the gamma value of the sample II was 0.9, whereas that of the sample I was 0.6. Further, the magenta image of the sample II was composed of considerably finer particles than in the case of the sample I.

EXAMPLE 2

Samples III and IV were prepared in the following manner:

Sample III

A mixture comprising 2.1 g. of the compound (10) and 15 g. of a magenta coupler 1-(2,4,6-trichlorophenyl)- 3-[(2,4-di-t-amylphenoxy)acetamide]benzamide -5-pyrazolone was dissolved in a solvent comprising 30 ml. of ethyl acetate and 15 cc. of dibutyl phthalate. The resulting solution was mixed with 20 ml. of a 10 percent aqueous Alkanol B solution and 200 ml. of a 5 percent aqueous gelatin solution. The mixed solution was emulsified and dispersed by means of a colloid mill. The resulting dispersion was dispersed in 1 kg. of a green-sensitive silver iodobromide emulsion, which was then coated on a cellulose triacetate base and dried to prepare the sample I.

Sample IV

Entirely the same operation as above was effected, except that the compound (10) was replaced by 7.2 g. [3 times the mole of the compound (10)] of p-lauroylamide-ω-(1-phenyl-5-tetrazolylthio)acetophenone, to prepare the sample IV.

These two samples III and IV were individually exposed through an optical wedge and then treated in the same manner as in Example 1. The results obtained were as follows:

| | Speed | Gamma |
|---|---|---|
| Sample III | 97 | 0.5 |
| Sample IV | 98 | 0.65 |

Thus, the two samples were same in speed, but the sample III was lower in gamma value than the sample IV despite the fact that the amount of the compound contained therein was one-third the amount of the control compound, and thus shows that the compound according to the present invention is higher in effectiveness. As to the graininess and sharpness of magenta image also, the compound according to the present invention was more excellent than the control compound. The control compound is the development inhibitor-releasable compound disclosed in Japanese Pat. Publication No. 22,514/1967.

EXAMPLE 3

Samples V and VI were prepared in the following manner:

Sample V

15 Grams of 2-[α-(2,4-di-t-amylphenoxy)-butyramide]-4,6-dichloro-5-methylphenol was added to 1 kg. of a red-sensitive silver iodobromide emulsion, which was then coated on a triacetate base to form a red-sensitive emulsion layer. Subsequently, a green-sensitive silver halide emulsion containing 3 g. of the compound (14) and 20 g. of 1-(2,4,6-trichlorophenyl)-3- 3-[α-(2,4-di-tertamylphenoxy)acetamide]benzamide -5-pyrazolone was coated on said emulsion layer and dried to prepare the sample V.

Sample VI

Entirely the same operation as above was effected, except that the compound (14) was not used, to prepare the sample VI as a control.

These two samples V and VI were individually exposed through an optical wedge to each of red light and white light, and then treated in the same manner as in Example 1.

In the case of the sample VI, the gamma values of the cyan images formed by exposure to red and white light were substantially identical with each other. However, in the case of the sample V, the gamma value of the cyan image formed by exposure to white light was obviously lower than that of the image formed by exposure to red light. This indicates that a development inhibitor, which was released from the compound (14) by exposure of the sample V to white light, diffused in the lower red-sensitive layer, with the result that the development of said red-sensitive layer was inhibited to lower the gamma value of the image.

EXAMPLE 4

0.8 Gram of a coupler disodium salt of 1-phenyl-3-(3,5-disulfo-benzamide)-4-(n-octadecyloxyphenylazo)-5-pyrazolone was dispersed at room temperature in 40 cc. of water with stirring to form a dispersion. The dispersion was incorporated with 5 cc. of a 10 percent sodium hydroxide solution, and then poured at 40°C. into a mixed solution comprising 100 cc. of a 10 percent gelatin solution and 8 cc. of a 5 percent Alkanol B solution. The resulting liquid was further incorporated with 1 cc. of a 7 percent saponin solution, adjusted to pH 6.8, charged with 8 cc. of a silver iodobromide emulsion, stirred for 2 minutes, allowed to stand at 40°C. for 30 minutes and then filtered. The thus prepared silver iodobromide emulsion was coated on a triacetate base, and the resulting emulsion layer was fogged by exposure for 30 seconds to a 40 watt-lamp positioned at a distance of 1.5 m.

On the other hand, 0.5 g. of the compound (8) was added to a mixture comprising 0.5 cc. of 2,4-di-namylphenol and 0.8 cc. of dimethylformamide, and the resulting mixture was heated with stirring at 80°C. to form a solution. This solution was added at 40°C. to a mixed solution comprising 20 cc. of a 10 percent gelatin solution and 2 cc. of a 5 percent Alkanol B solution, and then subjected 5 times to a colloid mill to form a dispersion. The residual dispersion in the mill was washed out of the mill with 8 cc. of water and 2 cc. of a 7 percent saponin solution, and combined with the aforesaid dispersion. Subsequently, the dispersion was charged with 10 cc. of a silver chlorobromide emulsion, stirred for 2 minutes and then allowed to stand at 40°C. for 30 minutes to form an emulsion.

The thus formed emulsion was coated on the aforesaid fogged emulsion layer to prepare a diffusion transfer type photographic material. This photographic material was exposed, contacted with an image-receiving material prepared by coating on a film a gelatin solution comprising 0.5 g. of cetyl-trimethylammonium bromide and 25 cc. of a 10 percent gelatin solution, and developed with a developer of the following composition:

| | |
|---|---|
| Sodium carbonate | 20.0 g. |
| Sodium hexamethaphosphate | 2.0 g. |
| Benzyl alcohol | 10.0 g. |
| 3-Acetamido-4-amino-N,N-diethylaniline | 2.0 g. |
| Water to make (pH 11) | 1.0 liter |

With progress of the development, a development inhibitor was formed at the exposed portion, and diffused to the lower fogged-emulsion layer to inhibit the development of said layer at the corresponding portion. At the unexposed portion, therefore, the fogged emulsion layer was not inhibited from development, so that the developing agent coupled with the coupler to form a magenta dye. This magenta dye transferred imagewise to the mordant dye-containing image-receiving material to form a clear, positive magenta image.

EXAMPLE 5

On a cellulose triacetate base, coating liquids of the compositions shown below were coated in order (weight per 900 cm²), thereby preparing a sample. 1. A red-sensitive silver iodobromide emulsion containing 440 mg. of gelatin and 174 mg. of silver halide:

The emulsion further contained 26.3 mg. of 1-hydroxy-4'-(4-t-butylphenoxy)-4-phenylazo-2-naphthanilide and 32.7 mg. of 1-hydroxy-N-[α-(2,4-di-tert-amylphenoxy)butyl]-2-naphthamide as couplers, and 7 mg. of the compound (8) as a development inhibitor-releasable compound. 2. A gelatin inter layer-forming liquid containing 83 mg. of gelatin and 3 mg. of dioctyl hydroquinone. 3. A green-sensitive silver iodobromide emulsion containing 400 mg. of gelatin and 243 mg. of silver halide.

The emulsion further contained 24.5 mg. of 1-(2,4,6-trichlorophenyl)-3- 3-[α-(2,4-di-t-amylphenoxy)acetamide]benzamide -4-(4'-methoxyphenylazo)-5-pyrazolone and 24.3 mg of 1-(2,4,6-trichlorophenyl)-3- 3-[α-(2,4-di-t-amylphenoxy)-acetamide]benzamide -5-pyrazolone as couplers, 7 mg. of the compound (8) as a development inhibitor-releasable compound, and 3.5 mg. of dioctyl hydroquinone as an anti-stain agent. 4. A gelatin inter layer-forming liquid containing 837 mg. of gelatin and 3 mg. of dioctyl hydroquinone. 5. A blue-sensitive silver iodobromide emulsion containing 200 mg. of gelatin and 62 mg. of silver halide.

The emulsion further contained 102.5 mg. of N-(p-benzoylacetamidobenzenesulfonyl)-N-(γ-phenylpropyl)-p-toluidine as a coupler, and 1.6 mg. of dioctyl hydroquinone as an anti-stain agent.

On the other hand, a control sample was prepared in the same manner as above, except that the compound (8) was not contained in the red-sensitive and green-sensitive emulsions.

These two samples were individually exposed through an optical wedge and then developed at 24°C. for 10 minutes with a developer of the following composition:

| | |
|---|---|
| Anhydrous sodium sulfite | 2.0 g. |
| N-Ethyl-N-β-methanesulfonamidoethyl-3-methyl-4-aminoaniline sulfate | 5.0 g. |
| Sodium carbonate | 50.0 g. |
| Sodium bromide | 0.9 g. |
| Sodium hydroxide | 4.0 g. |
| Sodium hexamethaphosphate | 0.5 g. |
| Benzyl alcohol | 4.0 ml. |
| Water to make | 1.0 liter |

Subsequently, the samples were subjected to ordinary bleach-fixing.

As the result, the former sample containing the compound (8) was not only more excellent in sharpness and graininess of image but also less in fog than the control sample.

EXAMPLE 6

A commercially available internal color photographic film was exposed through an optical wedge and then developed at 20°C. for 10 minutes with a color developer of the following composition:

| | |
|---|---|
| N-Ethyl-N-β-methanesulfonamidoethyl-3-methyl-4-aminoaniline sulfate | 5.0 g. |
| Sodium sulfite (anhydrous) | 2.0 g. |
| Benzyl alcohol | 3.8 g. |
| Sodium carbonate (monohydrate) | 50.0 g. |
| Potassium bromide | 1.0 g. |
| Potassium hydroxide | 0.55 g. |
| Compound (9) | 1.5 g. |
| Water to make | 1.0 liter |

Subsequently, the film was subjected to ordinary bleaching, fixing, water-washing, stabilizing and drying treatments to prepare a sample.

For comparison, the same color photographic film as above was developed with the same developer as above, except that the compound (9) was excluded, and then subjected to the same treatments as above to prepare a control sample.

Due to prominent image effects provided by the compound used, the sample according to the present invention was not only more excellent in sharpness and graininess of image but also more brilliant in color than the control sample.

What we claim is:

1. A process for developing an imagewise exposed, light-sensitive silver halide photographic material which comprises developing the photographic material in the presence of a compound having the general formula:

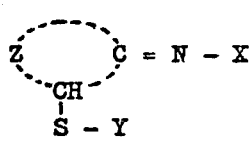

wherein Z is an atomic grouping necessary to form a 5, 6 or 7 membered carbocyclic ring; Y is a group which, when the sulfur atom of the thioether linkage is released, forms together with said sulfur atom a compound having a development-inhibiting action; and X is a hydroxyl group or a substituted or nonsubstituted amino group.

2. A process for developing a light-sensitive silver halide photographic material according to claim 1, wherein the compound of said formula in which X is a hydroxyl group is used.

3. A process for developing a light-sensitive silver halide photographic material according to claim 1, wherein to compound of said formula in which Z is an atomic grouping necessary to form the 5-membered carbocyclic ring is used.

4. A process for developing a light-sensitive silver halide photographic material according to claim 1, wherein the compound of said formula in which Z is an atomic grouping necessary to form the 5-membered carbocyclic ring and X is a hydroxyl group is used.

5. A process for developing a light-sensitive silver halide photographic material according to claim 3, wherein the compound of said formula in which Z is substituted by a phenyl or substituted phenyl group is used.

6. A process according to claim 1 wherein said ring is indanone, benzocyclohexenone or benzocycloheptenone.

7. A process according to claim 1 wherein said carboxylic ring has at least one substituent taken from the class consisting of alkyl, aryl, alkoxy, aryloxy and halogen.

8. A process according to claim 6 wherein said ring has at least one substituent taken from the class consisting of alkyl, aryl, alkoxy, aryloxy and halogen.

9. A process according to claim 1 wherein Y is an allylmercapto compound, a heterocyclic compound, a thioglycolic acid series compound, cystein or glutathione.

10. A process according to claim 9 wherein Y is a mercaptotetrazole compound, a mercaptothiazole compound, a mercaptooxadiazole compound, a mercaptopiperadine compound, a mercaptothiadiazole compound, a mercaptotriazine compound, a mercaptotriazole compound, or a mercaptobenzene compound.

11. A process according to claim 10 wherein Y is 1-phenyl-2-mercaptotetrazole, 1-nitrophenyl-5-mercaptotetrazole, 1-naphthyl-5-mercaptotetrazole, 2-mercaptobenzothiazole, 2-mercaptonaphthothiazole, 2-mercaptothiadiazolotriazole, 1-mercapto-2-benzoic acid, 1-mercapto-2-nitrobenzene, or 1-mercapto-3-heptadecanoylaminobenzene.

12. A process according to claim 1 wherein said compound is taken from the class consisting of

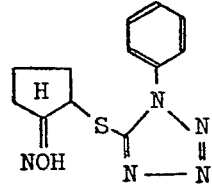

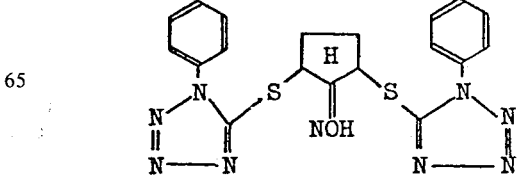

17
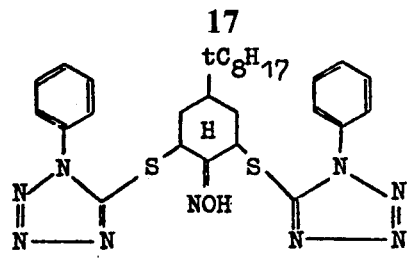
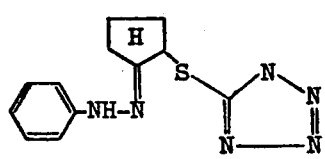
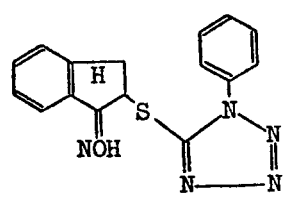
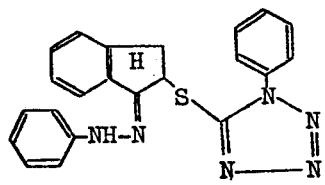
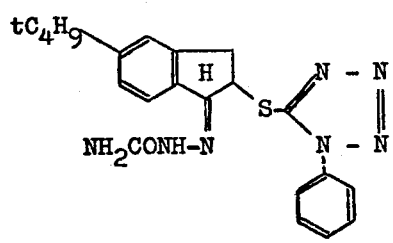
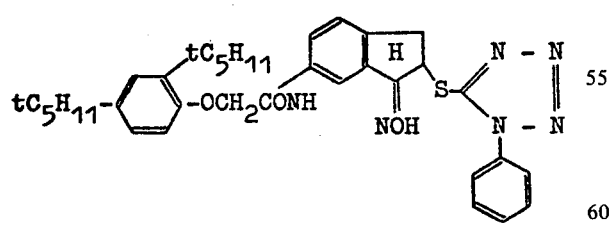
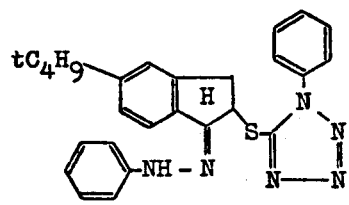
18
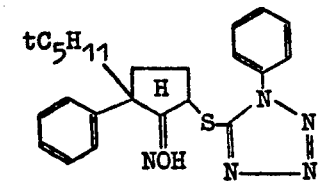
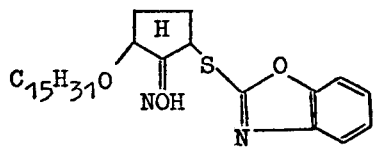
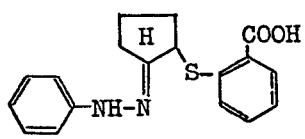
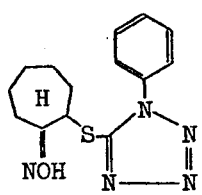
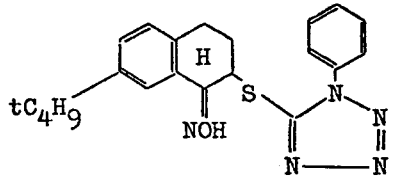
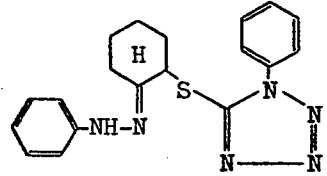
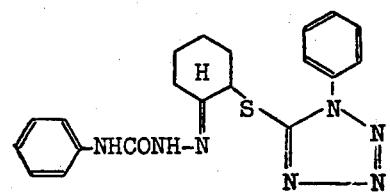
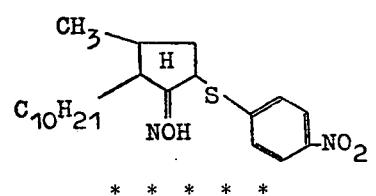
* * * * *